US00PP31439P2

(12) United States Plant Patent
van der Meer

(10) Patent No.: US PP31,439 P2
(45) Date of Patent: Feb. 11, 2020

(54) ***ASTILBE* PLANT NAMED 'HARVANDERMEERRUBYRED'**

(50) Latin Name: *Astilbe chinensis*
Varietal Denomination: Harvandermeerrubyred

(71) Applicant: Hans van der Meer, Nieuwe Wetering (NL)

(72) Inventor: Hans van der Meer, Nieuwe Wetering (NL)

(73) Assignee: Compass Plants B.V., Hillegom (NL)

( * ) Notice: Subject to any disclaimer, the term of this patent is extended or adjusted under 35 U.S.C. 154(b) by 0 days.

(21) Appl. No.: 16/350,790

(22) Filed: Jan. 12, 2019

(51) Int. Cl.
*A01H 5/02* (2018.01)
*A01H 6/80* (2018.01)

(52) U.S. Cl.
USPC ..... Plt./407

(58) Field of Classification Search
USPC ..... Plt./407
See application file for complete search history.

*Primary Examiner* — Susan McCormick Ewoldt
(74) *Attorney, Agent, or Firm* — C. A. Whealy

(57) ABSTRACT

A new and distinct cultivar of *Astilbe* plant named 'Harvandermeerrubyred', characterized by its tall, broadly upright and mounding plant habit; vigorous growth habit; dark green-colored leaves; freely and uniformly flowering habit; dark red purple-colored flowers on upright and strong peduncles; and good container and garden performance.

2 Drawing Sheets

Botanical designation: *Astilbe chinensis.*

Cultivar denomination: 'HARVANDERMEERRUBYRED'.

BACKGROUND OF THE INVENTION

The present, invention relates to a new and distinct cultivar of *Astilbe*, botanically known as *Astilbe chinensis* and hereinafter referred to by the name 'Harvandermeerrubyred'.

The new *Astilbe* plant is a product of a planned breeding program conducted by the Inventor in Nieuwe Wetering, The Netherlands. The objective of the breeding program was to create new uniform and freely flowering *Astilbe* plants with attractive leaf and flower coloration.

The new *Astilbe* plant originated from an open-pollination in 2011 in Nieuwe Wetering, The Netherlands, of *Astilbe chinensis* 'Harvandermeer', not patented, as the female, or seed, parent with an unknown *Astilbe chinensis* seedling selection as the male, or pollen, parent. The new *Astilbe* plant was discovered and selected by the Inventor as a single flowering plant from within the progeny of the stated open-pollination in a controlled greenhouse environment in Nieuwe Wetering, The Netherlands during the summer of 2013.

Asexual reproduction of the new *Astilbe* plant by vegetative divisions in a controlled nursery environment in Nieuwe Wetering, The Netherlands since December, 2013, has shown that the unique features of this new *Astilbe* plant are stable and reproduced true to type in successive generations.

SUMMARY OF THE INVENTION

Plants of the new *Astilbe* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Harvandermeerrubyred'. These characteristics in combination distinguish 'Harvandermeerrubyred' as a new and distinct *Astilbe* plant:

1. Tall, broadly upright and mounding plant habit.
2. Vigorous growth habit.
3. Dark green-colored leaves.
4. Freely and uniformly flowering habit.
5. Dark red purple-colored flowers on upright and strong peduncles.
6. Good container and garden performance.

Plants of the new *Astilbe* differ primarily from plants of the female parent, 'Harvandermeer', in the following characteristics:

1. Plants of the new *Astilbe* are taller than plants of 'Harvandermeer'.
2. Inflorescences of plants of the new *Astilbe* are larger than inflorescences of plants of 'Harvandermeer'.
3. Flowers of plants of the new *Astilbe* are dark red purple in color whereas flowers of plants of 'Harvandermeer' are dark pink in color.

Plants of the new *Astilbe* can be compared to plants of *Astilbe chinensis* 'Vision in Red', disclosed in U.S. Plant Pat. No. 11,965. In side-by-side comparisons, plants of the new *Astilbe* and 'Vision in Red' differ in the following characteristics:

1. Plants of the new *Astilbe* are taller than plants of 'Vision in Red'.
2. Leaves of plants of the new *Astilbe* are darker green in color than leaves of plants of 'Vision in Red'.
3. Inflorescences of plants of the new *Astilbe* are larger than inflorescences of plants of 'Vision in Red'.
4. Flowers of plants of the new *Astilbe* are dark red purple in color whereas flowers of plants of 'Vision in Red' are purple in color.

BRIEF DESCRIPTION OF THE PHOTOGRAPHS

The accompanying colored photographs illustrate the overall appearance of the new *Astilbe* plant showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet is a side perspective view of a typical flowering plant of 'Harvandermeerrubyred' grown in a container.

The photograph on the second sheet is a close-up view of typical inflorescences of 'Harvandermeerrubyred'.

DETAILED BOTANICAL DESCRIPTION

The aforementioned photographs and following observations, measurements and values describe plants grown during the spring and early summer in 19-cm containers in an outdoor nursery in Nieuwe Wetering, The Netherlands and under cultural practices typical of commercial *Astilbe* production. During the production of the plants, day temperatures ranged from 25° C. to 30° C. and night temperatures ranged from 15° C. to 20° C. Plants were one year old when the photographs and description were taken. In the following description, color references are made to The Royal Horticultural Society Colour Chart, 2015 Edition, except where general terms of ordinary dictionary significance are used.

Botanical classification: *Astilbe chinensis* 'Harvandermeerrubyred'.

Parentage:

*Female, or seed, parent.*—*Astilbe chinensis* 'Harvandermeer', not patented.

*Male, or pollen, parent.*—Unknown *Astilbe chinensis* seedling selection, not patented.

Propagation:

*Type.*—By vegetative divisions.

*Time to initiate roots.*—About three weeks at temperatures about 20° C.

*Root description.*—Thick, fleshy; typically brown in color, actual color of the roots is dependent on substrate composition, water quality, fertilizer type and formulation.

*Rooting habit.*—Freely branching; dense.

Plant description:

*Plant form and growth habit.*—Herbaceous perennial; tall, broadly upright and mounding plant form with inflorescences held above the foliar plane; flowering stems and leaves basal; freely flowering with numerous basal branches developing per plant, dense and bushy; vigorous growth habit; and freely and uniformly flowering habit.

*Growth rate.*—Rapid; from divisions, about six months are required to produce fully-grown flowering plants in containers.

*Plant height* (*soil level to top of foliar plane*).—About 51 cm.

*Plant height* (*soil level to top of inflorescences*).—About 87.9 cm.

*Plant width* (*spread*).—About 92.5 cm.

*Stem description.*—Length: About 46.5 cm. Diameter: About 3.5 mm. Internode length: About 18 cm. Strength: Strong. Aspect: Erect to about 5° from vertical. Texture and luster: Moderately pubescent; glossy. Color, developing: Close to 152B to 152C. Color, developed: Close to between 145A and 152A.

Leaf description:

*Arrangement.*—Alternate; biternately compound; about 39 leaflets per leaf.

*Leaf length* (*excluding petiole*).—About 30.6 cm.

*Leaf width.*—About 34.8 cm.

*Terminal leaflet length.*—About 7.4 cm.

*Terminal leaflet width.*—About 4.1 cm.

*Lateral leaflet length.*—About 5.3 cm.

*Lateral leaflet width.*—About 2.9 cm.

*Leaflet shape.*—Elliptic.

*Leaflet apex.*—Apiculate.

*Leaflet base.*—Attenuate.

*Leaflet margin.*—Biserrate.

*Leaflet texture and luster, upper and lower surfaces.*—Moderately pubescent; slightly rugose; slightly glossy.

*Leaflet venation pattern.*—Pinnate.

*Leaflet color.*—Developing leaflets, upper surface: Close to between 137B and 146B. Developing leaflets, lower surface: Close to 146B. Fully expanded leaflets, upper surface: Close to NN137A; venation, close to 144B. Fully expanded leaflets, lower surface: Close to 147B; venation, close to 145A to 145B.

*Leaf petiole length.*—About 40.7 cm.

*Leaf petiole diameter.*—About 2.75 cm.

*Leaf and leaflet petiole strength.*—Strong.

*Leaf and leaflet petiole texture and luster, upper and lower surfaces.*—Moderately pubescent; glossy.

*Leaf and leaflet petiole color, upper surface.*—Close to 144A and 199A; at the nodes, close to 178B to 178C.

*Leaf and leaflet petiole color, lower surface.*—Close to 144B and 199A to 199B; at the nodes, close to 152A.

Flower description:

*Flower type and flowering habit.*—Single rotate flowers arranged on terminal compound panicles; flowers face upright, outward or downward depending on position on the inflorescence; panicles narrowly conical in shape; freely and uniformly flowering habit with about 1,500 flowers developing per inflorescence.

*Fragrance.*—Moderate; sweet and pleasant.

*Natural flowering season.*—Plants begin flowering about 13 weeks after planting; continuously flowering from late spring until late summer in The Netherlands.

*Postproduction longevity.*—Flowers last about ten days on the plant; flowers not persistent.

*Flower buds.*—Height: About 2 mm. Diameter: About 1.75 mm. Shape: Roughly globular. Texture and luster: Smooth, glabrous; matte. Color: Close to 59D fading towards the base to close to 146D.

*Inflorescence height.*—About 37.1 cm.

*Inflorescence diameter.*—About 11.2 cm.

*Flower diameter.*—About 1 cm.

*Flower depth.*—About 7 mm.

*Petals.*—Quantity per flower: Typically five in a single whorl. Length: About 6 mm. Lobe width: About 0.6 mm. Shape: Oblanceolate. Apex: Narrowly acute. Base: Narrowly cuneate. Margin: Entire. Texture and luster, upper and lower surfaces: Smooth, glabrous; matte. Color: Developing petals, upper and lower surfaces: Close to 59B. Fully expanded petals, upper and lower surfaces: Close to 64B fading towards the base to close to 64C; color becoming closer to 64C with development.

*Sepals.*—Quantity per flower: Typically five in a single whorl, fused towards the base forming a campanulate-shaped calyx. Length: About 2.5 mm. Width: About 1 mm. Shape: Broadly ovate. Apex: Acute. Base: Cuneate, fused. Margin: Entire. Texture and luster, upper and lower surfaces: Smooth, glabrous; matte. Color: Developing sepals, upper surface: Close to 62C; towards the margins, close to 63A. Developing sepals, lower surface: Close to 62C; towards the margins, close to 64C. Fully expanded sepals, upper surface: Close to 62D; towards the margins, close to 63B. Fully expanded sepals, lower surface: Close to 62D; towards the margins, close to 64D.

*Peduncles.*—Length: About 36.8 cm. Diameter: About 2.5 mm. Angle: Mostly erect. Strength: Strong. Texture and luster: Densely pubescent; slightly glossy. Color: Close to 152B.

*Pedicels.*—Length: About 0.75 mm. Diameter: About 0.5 mm. Angle: About 60° from peduncle axis. Strength: Moderately strong. Texture and luster: Moderately to densely pubescent; matte. Color: Close to 59D.

*Reproductive organs.*—Stamens: Quantity per flower: Typically twelve; anthers basifixed. Filament length: About 4 mm. Filament color: Close to 64C. Anther shape: Broadly ovate. Anther length: About 0.5 mm. Anther diameter: About 0.2 mm. Anther color: Close to 75D. Pollen amount: Moderate. Pollen color: Close to 76C. Pistils: Quantity per flower: Two. Pistil length: About 3 mm. Stigma diameter: About 0.1. mm. Stigma shape: Club-shaped. Stigma color: Close to 64B. Style length: About 2.75 mm. Style color: Close to 64C. Ovary color: Close to 64C.

*Seeds and fruits.*—To date, seed and fruit development have not been observed on plants of the new *Astilbe*.

Pathogen & pest resistance: To date, plants of the new *Astilbe* have not been noted to be resistant to pathogens and pests common to *Astilbe* plants.

Garden performance: Plants of the new *Astilbe* have been observed to have good garden performance and tolerate rain, wind and high temperatures of about 35° C. Additionally, plants of the new *Astilbe* have been observed to be suitable for USDA Hardiness Zones 5 through 10.

It is claimed:

1. A new and distinct *Astilbe* plant named 'Harvandermeerrubyred' as illustrated and described.

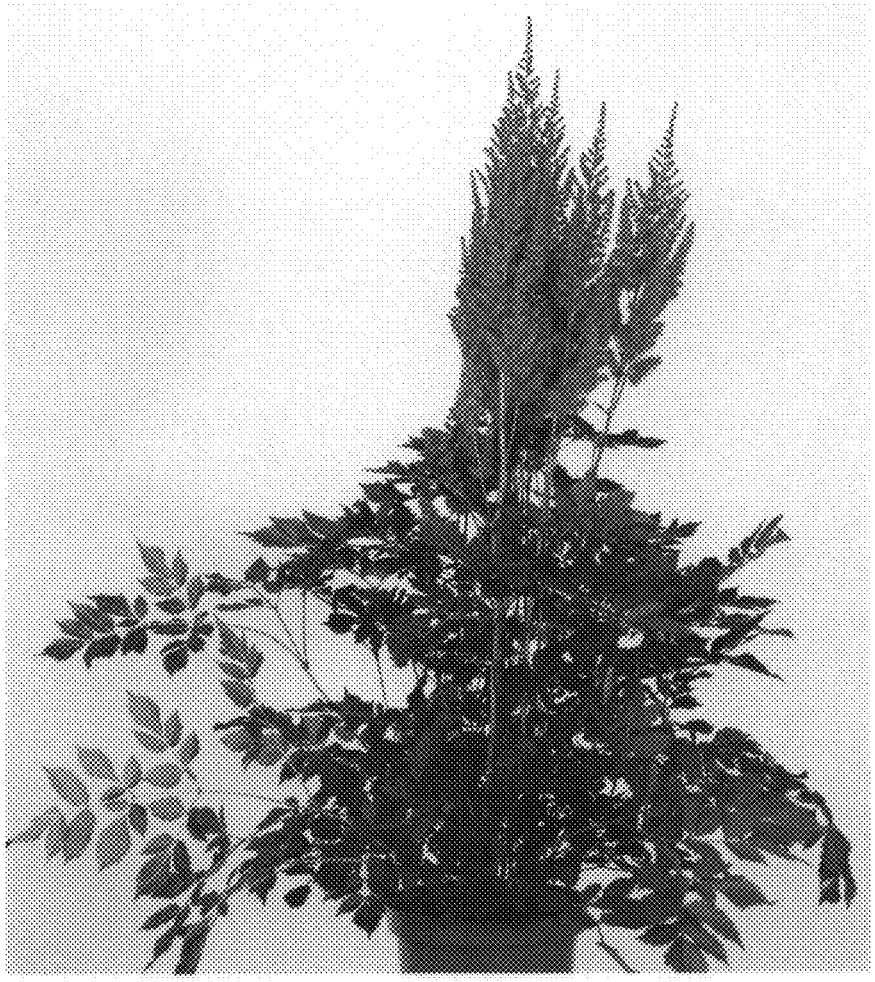

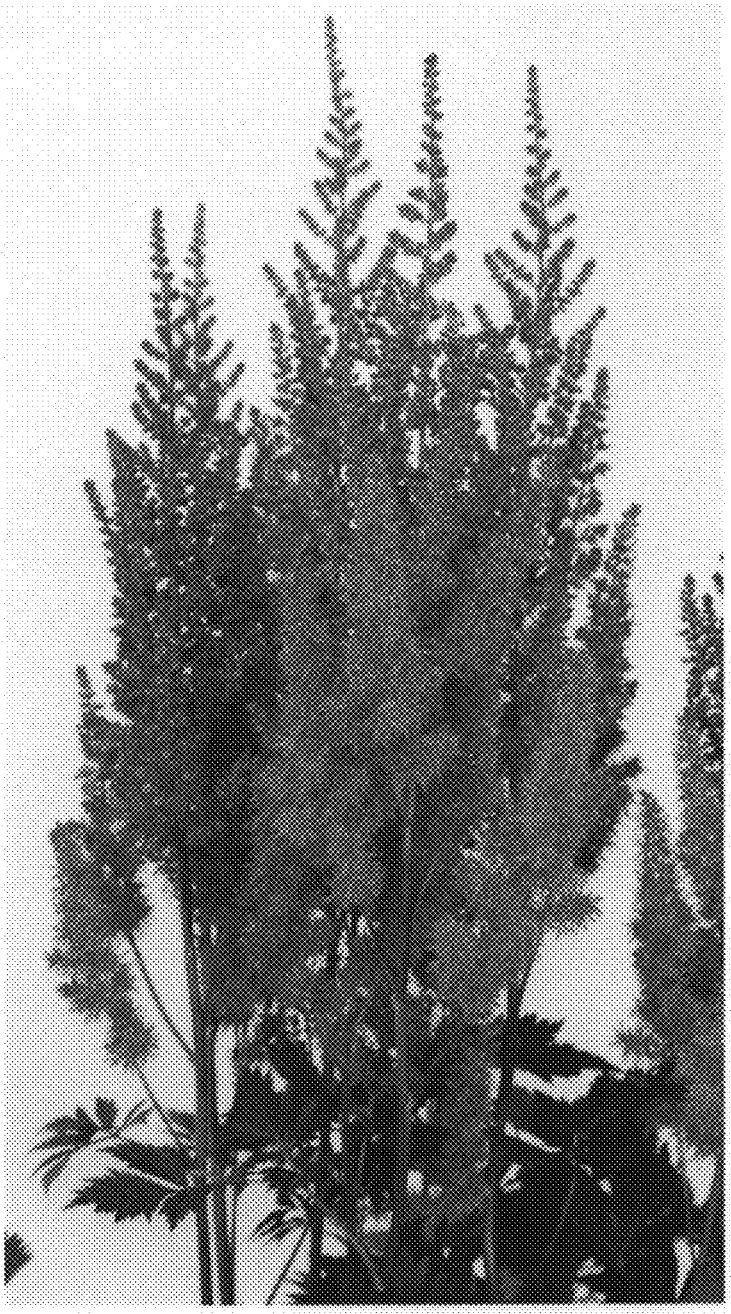

* * * * *